US010213166B2

(12) United States Patent
Levesque et al.

(10) Patent No.: US 10,213,166 B2
(45) Date of Patent: *Feb. 26, 2019

(54) SYSTEMS AND METHODS FOR PROVIDING ENHANCED HAPTIC FEEDBACK

(71) Applicant: IMMERSION CORPORATION, San Jose, CA (US)

(72) Inventors: Vincent Levesque, Montreal (CA); Abdelwahab Hamam, Montreal (CA); Juan Manuel Cruz-Hernandez, Montreal (CA); Vahid Khoshkava, Montreal (CA)

(73) Assignee: IMMERSION CORPORATION, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/709,106

(22) Filed: Sep. 19, 2017

(65) Prior Publication Data

US 2018/0000429 A1    Jan. 4, 2018

Related U.S. Application Data

(63) Continuation of application No. 14/587,135, filed on Dec. 31, 2014, now Pat. No. 9,763,628.

(51) Int. Cl.
*A61B 5/00*    (2006.01)
*G06F 3/01*    (2006.01)

(52) U.S. Cl.
CPC .......... *A61B 5/7455* (2013.01); *G06F 3/016* (2013.01)

(58) Field of Classification Search
CPC . G06F 3/01; G06F 3/011; G06F 3/014; G06F 3/016; G06F 3/018; A61B 5/7455; A61B 5/7475; A61B 5/748; A61B 5/7485; A61B 5/00; G08B 6/00
See application file for complete search history.

(56) References Cited

U.S. PATENT DOCUMENTS

| 9,763,628 B2 * | 9/2017 | Levesque ............... G06F 3/016 |
| 2007/0208130 A1 | 9/2007 | Sasahara et al. |
| 2008/0035207 A1 | 2/2008 | Lamers et al. |
| 2009/0195512 A1 * | 8/2009 | Pettersson ............ G06F 3/016 345/173 |
| 2009/0296341 A1 * | 12/2009 | Eldershaw ............ G06F 1/1626 361/679.43 |
| 2011/0250958 A1 | 10/2011 | Aarts et al. |
| 2013/0116340 A1 | 5/2013 | Furukawa et al. |
| 2014/0320396 A1 | 10/2014 | Modarres et al. |
| 2014/0337725 A1 | 11/2014 | Smith et al. |
| 2014/0362014 A1 | 12/2014 | Ullrich et al. |

(Continued)

FOREIGN PATENT DOCUMENTS

WO    2011/093873    8/2011

OTHER PUBLICATIONS

European Search Report (EP 15202234.9) dated May 19, 2016 (7 pages).

(Continued)

*Primary Examiner* — Van T Trieu
(74) *Attorney, Agent, or Firm* — Miles & Stockbridge P.C.

(57) ABSTRACT

A system includes a haptic output device constructed and arranged to generate a haptic effect to a user of the system, and a chemical delivery device constructed and arranged to deliver a chemical to the user of the system.

21 Claims, 4 Drawing Sheets

(56) References Cited

U.S. PATENT DOCUMENTS

2015/0316985 A1 11/2015 Levesque et al.
2015/0370320 A1 12/2015 Connor

OTHER PUBLICATIONS

Lévêque et al., "Changes in Tactile Spatial Discrimination and Cutaneous Coding Properties by Skin Hydraftion in the Elderly," The Society for Investigative Dermatology, Inc., 2000, pp. 454-458.
Ou et al., bioPrint: An Automatic Desposition System for Bacteria Spore Actuators, UIST'14, Oct. 5-8, 2014, Honolulu, HI, USA, pp. 121-122.
Pohl, "Brave New Interactions: Performance-Enhancing Drugs for Human-Computer Interaction," CHI 2014, One of a CHInd, ON, Canada, pp. 835-843.

* cited by examiner

SYSTEMS AND METHODS FOR PROVIDING ENHANCED HAPTIC FEEDBACK

CROSS REFERENCE TO RELATED APPLICATION

This application is a continuation application of U.S. patent application Ser. No. 14/587,135, filed Dec. 31, 2014, issued as U.S. Pat. No. 9,763,628 on Sep. 19, 2017, the entire contents of which are incorporated herein by reference.

FIELD

The present invention is related to systems and method for providing enhanced haptic feedback.

BACKGROUND

Handheld device users often would like their devices to provide stronger haptic feedback, which may be difficult to accomplish due to size and power constraints of handheld devices. Handheld device designers generally try to produce the best haptic feedback possible within certain size and power constraints. In addition, some users of handheld devices have low tactile sensitivity and therefore may have difficulty feeling haptic effects. Audio or video feedback may be used to compensate for weak haptic feedback, or haptic notifications that may possibly be missed.

SUMMARY

There is a need to be able to enhance the haptic feedback that is felt by users of handheld devices.

According to an aspect of the invention, there is provided a system that includes a haptic output device constructed and arranged to generate a haptic effect to a user of the system, and a chemical delivery device constructed and arranged to deliver a chemical to the user of the system.

In an embodiment, the system further includes one or more processors configured to execute at least one computer program module comprising a determination module that, when executed by the one or more processors, determines when to initiate delivery of the chemical to change tactile sensitivity of the user and alter the haptic effect generated by the haptic output device.

In an embodiment, the chemical delivery device includes a reservoir constructed and arranged to hold the chemical, and a positive pressure device constructed and arranged to extract the chemical from the reservoir and deliver the chemical through an opening to the user.

In an embodiment, the chemical is selected from the group consisting of: a moisturizer, a topical anesthetic, a conductive gel, and a pH adjuster.

In an embodiment, the haptic output device includes the chemical delivery device, and the chemical generates the haptic effect. In an embodiment, the haptic effect is a sensation selected from the group consisting of a burning sensation, a warming sensation, a cooling sensation, an itching sensation, and a numbing sensation.

In an embodiment, the system is in the form of a handheld device selected from the group consisting of a tablet, a smartphone, and a game controller.

In an embodiment, the system further includes a sensor configured to sense a condition of the user's skin. In an embodiment, the condition is humidity.

According to an aspect of the invention, there is provided a method to alter a haptic effect felt by a user of an electronic device. The method includes delivering a chemical with a chemical delivery device to the user of the electronic device to change tactile sensitivity of the user of the electronic device, and generating the haptic effect to the user of the electronic device with a haptic output device.

In an embodiment, the method further includes sensing a condition of the user's skin with a sensor, and determining whether to initiate delivery of the chemical to the user of the electronic device based on the sensed condition.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following Figures are illustrated to emphasize the general principles of the present disclosure and are not necessarily drawn to scale. Reference characters designating corresponding components are repeated as necessary throughout the Figures for the sake of consistency and clarity.

DETAILED DESCRIPTION

Figure 1:
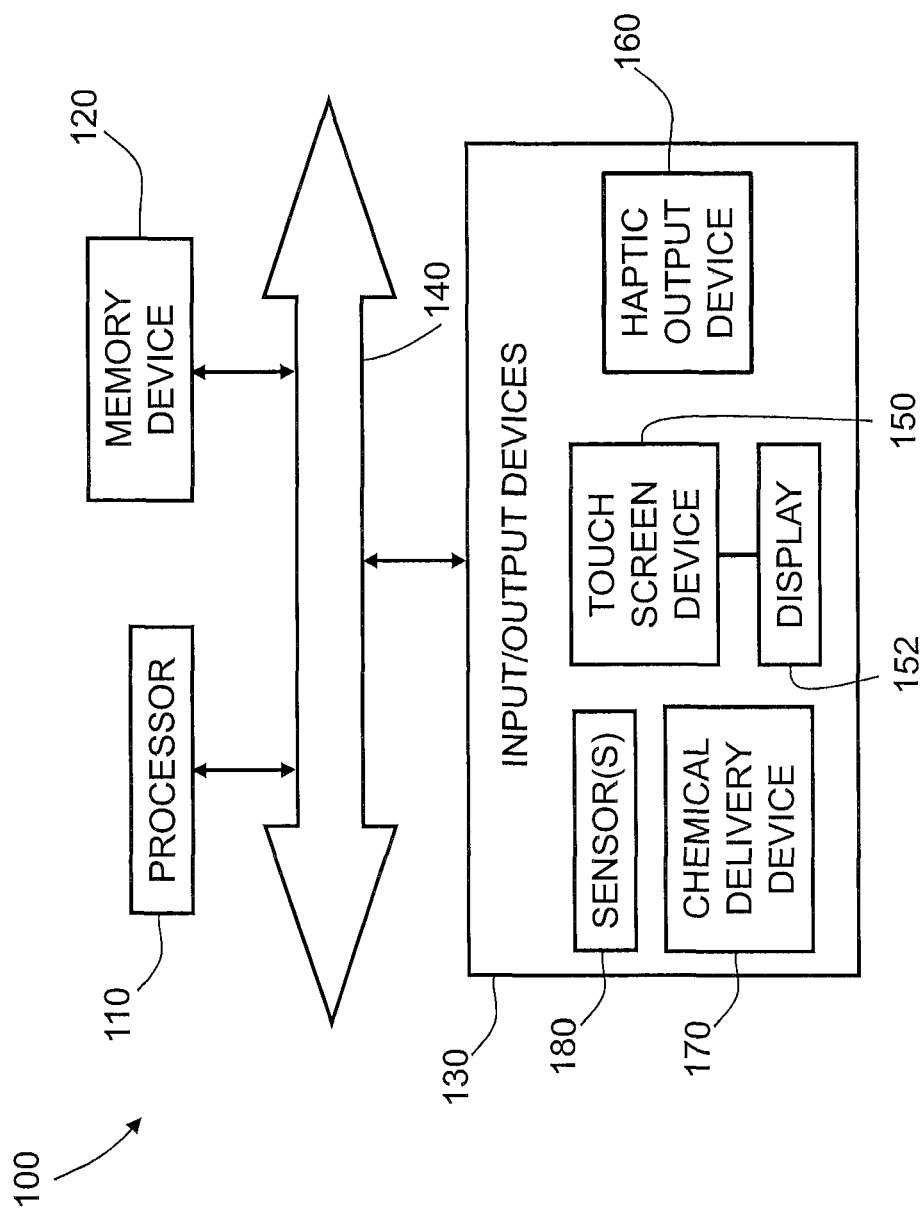
FIG. 1 is a schematic illustration of a system in accordance with embodiments of the invention.

FIG. 1 is a schematic illustration of a system 100 in accordance with an embodiment of the invention. The system 100 may be any electronic device, such as a desktop computer, laptop computer, electronic workbook, electronic handheld device (such as a mobile phone, smartphone, gaming device, personal digital assistant ("PDA"), portable e-mail device, portable Internet access device, calculator, etc.), kiosk (such as an automated teller machine, ticket purchasing machine, etc.), printer, point-of-sale device, game controller, wearable device, or other electronic device. As illustrated, the system 100 includes a processor 110, a memory device 120, and input/output devices 130, which are interconnected via a bus 140. In an embodiment, the input/output devices 130 may include a touch screen device 150, a haptic output device 160, a chemical delivery device 170, one or more sensors 180, and/or other input devices that receive input from a user of the system 100 and output devices that output information or chemicals to the user of the system 100. In an embodiment, the system 100 may be a handheld electronic device that includes all of the components illustrated in FIG. 1 in a single integrated device. In an embodiment, two or more of the components illustrated in FIG. 1 may be co-located in the same electronic device. In an embodiment, each component illustrated in FIG. 1 may be separately located in an different electronic device.

In addition to the touch screen device 150 and the haptic output device 160, the input/output devices 130 may also include specific input mechanisms and output mechanisms. For example, the input mechanisms may include such devices as keyboards, keypads, cursor control devices (e.g., computer mice), other data entry devices, such as styluses, or an audio receiver, such as a microphone. Output mechanisms may include a computer monitor, virtual reality display device, audio output device, such as a speaker, printer, or other peripheral devices. The input/output devices 130 may include mechanisms that are designed to not only receive input from a user, but also provide feedback to the user, such as many examples of touch screen devices.

The touch screen device 150 may be configured as any suitable user interface or touch/contact surface assembly. The touch screen device 150 may be any touch screen, touch pad, touch sensitive structure, computer monitor, laptop display device, workbook display device, kiosk screen, portable electronic device screen, or other suitable touch sensitive device. The touch screen device 150 may be configured for physical interaction with a user-controlled device, such as a stylus, finger, etc. In some embodiments, the touch screen device 150 may include at least one output device and at least one input device. For example, the touch screen device 150 may include the visual display 152 configured to display, for example, images and a touch sensitive screen comprising at least one sensor superimposed thereon to receive inputs from a user's finger or stylus controlled by the user. The visual display 152 may include a high definition display screen.

In various embodiments, the haptic output device 160 is configured to provide haptic feedback to the user of the system 100 while the user is in contact with a least a portion of the system 100. For example, the haptic output device 160 may provide haptic feedback to the touch screen device 150 itself to impose a haptic effect when the user is in contact with the touch screen device 150 and/or to another part of the system 100, such as a housing containing at least the input/output devices 130. The haptic effects may be used to enhance the user experience when interacting with the system 100.

The haptic feedback provided by the haptic output device 160 may be created with any of the methods of creating haptic effects, such as vibration, deformation, kinesthetic sensations, electrostatic or ultrasonic friction, etc. In an embodiment, the haptic output device 160 may include an actuator, for example, an electromagnetic actuator such as an Eccentric Rotating Mass ("ERM") in which an eccentric mass is moved by a motor, a Linear Resonant Actuator ("LRA") in which a mass attached to a spring is driven back and forth, or a "smart material" such as piezoelectric materials, electro-active polymers, such as ionic or electronic based electroactive polymers, shape member polymers, smart hydrogels, or shape memory alloys, a macro-composite fiber actuator, an electro-static actuator, an electro-tactile actuator, a nanocomposite actuator, a pneumatic-based actuator and/or another type of actuator that provides a physical feedback such as vibrotactile feedback. The haptic output device 160 may include non-mechanical or non-vibratory devices such as those that use electrostatic friction (ESF), ultrasonic friction (USF), or those that induce acoustic radiation pressure with an ultrasonic haptic transducer, or those that use a haptic substrate and a flexible or deformable surface, or those that provide thermal effects, or those that provide projected haptic output such as a puff of air using an air jet, and so on. Multiple haptic output devices 160 may be used to generate different haptic effects, as discussed in further detail below.

Figure 2:
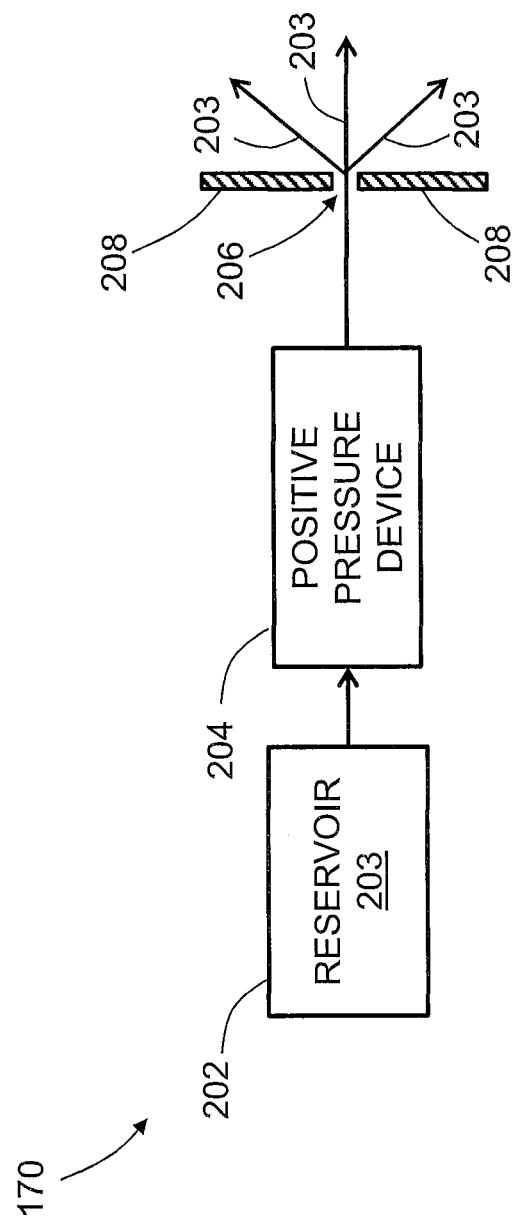
FIG. 2 is a schematic illustration of a chemical delivery device of the system of FIG. 1, in accordance with an embodiment of the invention.

An embodiment of the chemical delivery device 170 is schematically illustrated in FIG. 2. In the illustrated embodiment, the chemical delivery device 170 includes a reservoir 202 constructed and arranged to hold a chemical represented by 203. The chemical 203 may be a touch-enhancing chemical or any chemical that can alter a person's sensitivity to the haptic effects that are generated by the haptic output device 160, or the chemical 203 may be used to provide a haptic effect, as described in further detail below. The chemical 203 may come in the form of a powder, a liquid, a cream, a gel, or a gas, for example.

In an embodiment, the chemical 203 may be a moisturizer, talc, an antiperspirant or any other chemical that affects moisture in the skin. It is known that a moisturizer may improve the tactile sensitivity of, for example, an elderly person. Also, talc and an antiperspirant may reduce the humidity of the skin and affect tactile sensitivity as well. It is also known that dry skin and calluses also reduce tactile sensitivity, and chemicals that reverse the condition of dry skin or heal calluses may also be used to improve tactile sensitivity. Alterations of the pH of the skin may also affect tactile sensitivity, so a chemical that causes a change in the pH of the skin may also be used in an embodiment of the invention. In an embodiment, the chemical 203 may include a substance that may increase blood flow, such as arginine cream and cellulite cream, which may improve tactile sensitivity.

In an embodiment, the chemical 203 may be in the form of a gel and/or include active ingredients that can clean the skin and remove dead skin cells, which may increase tactile sensitivity. In an embodiment, the chemical 203 may be a conductive gel that is typically used for electrodes and may affect the delivery of ESF or electrotactile stimuli. Gels and other viscous chemicals may also alter the sensation caused by mechanical vibration, such as by damping the vibrations or making a better mechanical contact.

It is also known that certain drugs, such as drugs containing amphetamines, including 3,4-methylenedioxy-methamphetamine may cause a hypersensitivity of the skin. Legal chemicals or drugs that cause a similar hypersensitivity may be used as the chemical 203 with embodiments of the invention. In an embodiment, a chemical or drug that is used to restore tactile sensitivity in patients with peripheral neuropathy may be used as the chemical 203 with embodiments of the invention.

In some embodiments of the invention, the chemical 203 may be used to alter the tactile sensitivity of the user in a manner that reduces the tactile sensitivity of the user, instead of enhancing the tactile sensitivity of the user. For example, in an embodiment, a topical anesthetic that reduces tactile sensitivity of or numbs the user's skin may be used to mask unwanted tactile sensations or to temporarily increase the level of difficulty in a game or to reflect the physical state of a game avatar.

In an embodiment, the chemical 203 may be selected to provide a certain tactile sensation to the user of the system, such as a warming or burning sensation, a cooling sensation, or an itching sensation. For example, capsaicin or muscle balm may be used to cause a burning sensation, and menthol, peppermint oil, alcohol, or aloe vera may be used to produce a sensation of cold. Chemicals found in poison ivy and itching powder may be used to cause an itching sensation or a mild irritation of the skin. Some chemicals may cause an exothermic reaction and warm up the skin. This sensation of warmth may be used directly as a haptic effect, or it may be used to alter tactile sensitivity, which varies with the temperature of the skin. Some chemicals may cause an endothermic reaction and cool the skin.

In an embodiment, the chemical 203 may be selected to alter the adherence of the skin and make the skin sticky or slippery, which may be used to make a surface of the system 100 in contact with the user feel sticky or slippery, depending on the context. In an embodiment, such a chemical may make a touchscreen or buttons of the input/output device(s) 130 of the system 100 described above feel sticky or slippery after touching the chemical 203. This may be done by controlling the moisture of the skin, as described above. This may also be done by delivering other chemicals, such as oils and adhesive substances. The effect caused by a particular chemical may be counteracted by delivering the opposite chemical (e.g., adhesive after oil) or by delivering a chemical that may "clean up" the first chemical (e.g., alcohol to dissolve adhesive, talc to absorb oil, etc.).

In an embodiment, the chemical 203 may have an odor that may indirectly affect the interpretation of tactile sensations. For example, a pleasant smell may lead to tactile sensations with a positive effect on the user.

The chemical delivery device 170 may also include a positive pressure device 204 that is constructed and arranged to deliver the chemical 203 from the reservoir 202 through an opening 206 of a wall 208 of the system 100 so that the chemical 203 can contact a user of the system 100 and alter the user's sensitivity to the haptic effects that are generated by the haptic output device 160. In an embodiment, the positive pressure device 204 may include a micropump and a microvalve that are configured to control the release of the chemical 203 from the reservoir 202. In an embodiment, the positive pressure device 204 may include a pneumatic system that is constructed and arranged to push the chemical out of the reservoir 202 and through the opening 206 when the user of the system 100 firmly holds or squeezes a part of the system 100 that includes the chemical delivery device 170. In an embodiment, the chemical 203 may be released from the reservoir 202 by osmotic pressure through a membrane having one or more pores.

In an embodiment, the chemical delivery device 170 may include a mechanism or a device that may facilitate or inhibit the release of the chemical 203. For example, a portion of the chemical delivery device 170 may be slightly heated or cooled to affect the release of the chemical 203. In an embodiment, the size of the pore(s) of the membrane though which the chemical 203 is released may be changed by heating the membrane or with another chemical, for example, and the chemical 203 may be released through the membrane if the pore size is changing. In an embodiment, a portion of the housing may be electrically charged to affect the release of the chemical 203.

Returning to FIG. 1, the processor 110 may be a general-purpose or specific-purpose processor or microcontroller for managing or controlling the operations and functions of the system 100. For example, the processor 110 may be specifically designed as an application-specific integrated circuit ("ASIC") to control output signals to the haptic output device 160 to provide haptic effects. The processor 110 may be configured to decide, based on predefined factors, whether the chemical 203 is delivered by the chemical delivery device 170 and/or what haptic effects are to be generated by the haptic output device 160 based on a haptic signal received or determined by the processor 110, the order in which the haptic effects are generated, and the magnitude, frequency, duration, and/or other parameters of the haptic effects. The processor 110 may also be configured to provide streaming commands that can be used to drive the haptic output device 160 for providing a particular haptic effect. In some embodiments, the processor 110 may actually be a plurality of processors, each configured to perform certain functions within the system 100. The processor 110 is described in further detail below.

The memory device 120 may include one or more internally fixed storage units, removable storage units, and/or remotely accessible storage units. The various storage units may include any combination of volatile memory and non-volatile memory. The storage units may be configured to store any combination of information, data, instructions, software code, etc. More particularly, the storage units may include haptic effect profiles, instructions for how the haptic output device 160 is to be driven, or other information for generating haptic effects. The storage units may include sensitivity profiles, instructions for how the chemical delivery device 170 is to be operated, or other information for delivering the chemical 203 to the user of the system 100.

Figure 3:
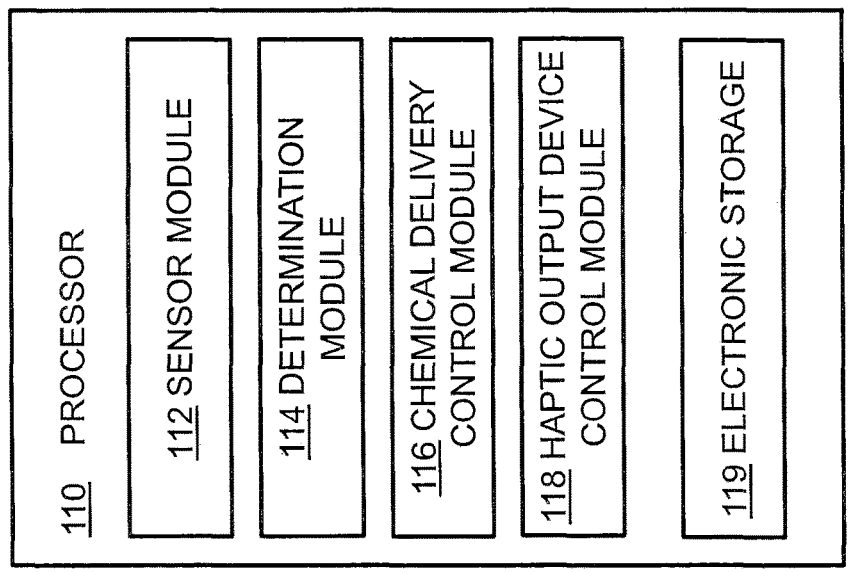
FIG. 3 is a schematic illustration of a processor of the system of FIG. 1, in accordance with an embodiment of the invention.

FIG. 3 illustrates an embodiment of the processor 110 in more detail. The processor 110 may be configured to execute one or more computer program modules. The one or more computer program modules may include one or more of a sensor module 112, a determination module 114, a chemical delivery control module 116, a haptic output device control module 118, and/or other modules. The processor 110 may also include electronic storage 119, which may be the same as the memory device 120 or in addition to the memory device 120. The processor 110 may be configured to execute the modules 112, 114, 116, and/or 118 by software, hardware, firmware, some combination of software, hardware, and/or firmware, and/or other mechanisms for configuring processing capabilities on processor 110.

It should be appreciated that although modules 112, 114, 116, and 118 are illustrated in FIG. 3 as being co-located within a single processing unit, in embodiments in which the processor 110 includes multiple processing units, one or more of modules 112, 114, 116, and/or 118 may be located remotely from the other modules. The description of the functionality provided by the different modules 112, 114, 116, and/or 118 described below is for illustrative purposes, and is not intended to be limiting, as any of the modules 112, 114, 116, and/or 118 may provide more or less functionality than is described. For example, one or more of the modules 112, 114, 116, and/or 118 may be eliminated, and some or all of its functionality may be provided by other ones of the modules 112, 114, 116, and/or 118. As another example, the processor 110 may be configured to execute one or more additional modules that may perform some or all of the functionality attributed below to one of the modules 112, 114, 116, and/or 118.

The sensor module 112 is configured to receive an input signal from the sensor associated with the touch screen device 150 that is generated when the sensor detects an input from a user of the system 100. In embodiments in which there are multiple sensors, the sensor module 112 is configured to receive and process input signals from the multiple sensors. The sensor module 112 may be configured to determine whether the sensed input is an intentional input or merely an inadvertent touch to the touch screen device 150 by comparing the strength of the input signal to a predetermined threshold strength that corresponds to an intentional input. In an embodiment the system 100, one of the sensors 180 may be configured to measure the moisture content, i.e. humidity, or pH of the user's skin as the user touches a part of the system 100. The sensor module 112 is also configured to send a signal to the determination module 114 for further processing.

The determination module 114 is configured to determine what was intended by the user when providing an input to the touch screen device 150. For example, the user may touch a certain location of the touch screen device 150 or provide a particular gesture to the touch screen device 150 that indicates that a certain function is to be performed by the system 100. The determination module 114 may be programmed with a library of predetermined gestures and touch locations on the touch screen device 150 so that when the user touches a particular location on the touch screen device 150 or provides a gesture to the touch screen device 150, the determination module 114 may determine a corresponding output. For example, in an embodiment in which the system 100 is a smartphone, the user may draw a symbol on the touch screen device 150 with his or her finger and the determination module 114 may determine that the drawn symbol corresponds to a particular command, such as unlocking the smartphone so that the user may freely interact with the smartphone. In an embodiment, the determination module 114 may be configured to receive a signal from a remote device, such as a timer, that provides an input to indicate that a haptic effect is to be generated, instead of or in addition to the signal received from the sensor module 112. In addition, the determination module 114 may also output a signal to the haptic output device control module 118 so that a haptic effect verifying the input has been detected and/or accepted may be provided to the user.

The determination module 114 is also configured to determine whether the humidity or pH of the user's skin that was measured by the sensor 180 is at a level that may be indicative that the user may have low tactile sensitivity and difficulty feeling the haptic effects that are generated by the haptic output device 160. If the determination module 114 determines that the tactile sensitivity is likely to be below a predetermined threshold, the determination module 114 may output a signal to the chemical delivery control module 116.

The chemical delivery control module 116 is configured to receive an output signal from the determination module 114 and send a signal to the chemical delivery device 170 to initiate delivery of the chemical 203, if the determination module 114 determines that the chemical 203 should be delivered to the user. The chemical delivery control module 116 may include a look-up table that provides parameters for the chemical delivery device 170, such as an amount (i.e. dose) of the chemical 203 to be delivered, and a duration of time over which the chemical 203 is to be delivered to the user.

The haptic output device control module 118 is configured to receive an output signal from the determination module 114 and determine the haptic effect to be generated by the haptic output device 160, based on the signal generated by the determination module 114. In an embodiment, the haptic output device control module 118 may be configured to receive a signal from a remote device, such as a timer, that provides an input to indicate that a haptic effect is to be generated, instead of or in addition to the signal received from the determination module 114. Determining the haptic effect may include determining the type of haptic effect and one or more parameters of the haptic effect, such as amplitude, frequency, duration, etc., of the haptic effect. In an embodiment, the touch screen device 150 includes a display surface, which may be rigid and configured to modulate its friction properties through, including but not limited to, electrostatic friction and ultrasonic surface vibration generated by a haptic output device 160, to give the user a feeling of surface relief (e.g., hills and valleys) when running a finger or stylus across the display that corresponds to the display image. In an embodiment, the haptic output device control module 118 may output a signal to the chemical delivery device 170 when the chemical 203 in the chemical delivery device 170 is to provide the haptic effect.

Figure 4B:
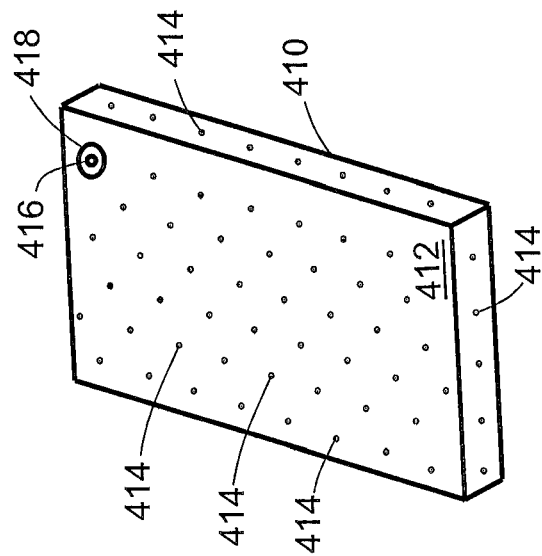
FIG. 4B schematically illustrates a rear perspective view of the handheld electronic device of FIG. 4A, in accordance with an embodiment of the invention.
Figure 4A:
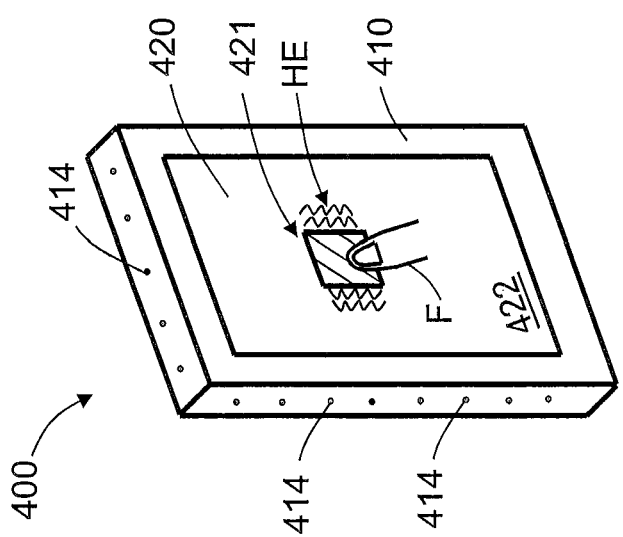
FIG. 4A schematically illustrates a front perspective view of an implementation of the system of FIG. 1 in the form of a handheld electronic device, in accordance with an embodiment of the invention.

FIGS. 4A and 4B illustrate an embodiment of the system 100 of FIG. 1 in the form of a handheld electronic device 400. The electronic device 400 may be a smartphone, a tablet, a game controller, etc. As illustrated in FIG. 4A, the electronic device 400 includes a housing 410 that supports a touchscreen 420 configured to display an image 421. A sensor 422 overlays a display of the touchscreen 420 and is configured to sense a touch input by the user's finger F on the touchscreen 420. A haptic effect HE may be generated in response to the touch input by a haptic output device, as described above.

As illustrated in FIG. 4B, the housing 410 also supports a sensor 412 that may cover the back and/or sides of the housing and be configured to sense a condition of the user's skin when the user holds the electronic device 400. In an embodiment, the sensor 412 is configured to sense the humidity of the user's skin. In an embodiment, the sensor 412 is configured to sense a pH of the user's skin. As also illustrated in FIG. 4B, the housing 410 includes a plurality of openings 414. The openings 414 may be constructed and arranged like the opening 206 illustrated in FIG. 2, and configured to deliver the chemical 203 to the user, if the determination module 114 determines that the chemical 203 should be delivered to the user to enhance the user's tactile sensitivity. In an embodiment, the chemical 203 may be delivered through the openings 414 to generate the haptic effect to the user.

Although a plurality of openings 414 are illustrated, in accordance with an embodiment of the invention, as few as one opening may be provided at a location that is easy to be located by the user. For example, in the embodiment illustrated in FIG. 4B, an opening 416 with a locating feature 418 may be provided in one corner of the housing 410 so that the user may easily locate the opening 416 in order to receive a dose of the chemical 203 for further interaction with the electronic device 400. The locating feature 418 may, for example, be in the form of a recess or a bump. In an embodiment, the chemical 203 delivered though the opening 416 or the plurality of openings 414 may be used to generate a haptic effect, such as burning, cooling, itching, or tingling, as discussed above.

In an embodiment, the housing 410 of the electronic device 400 may be configured to continuously deliver the chemical 203, especially if the chemical enhances tactile sensitivity, if the sensor 412 senses that the electronic device 400 is being held by the user. In an embodiment, the housing 410 itself may, for example, contain a material that reacts to the heat or humidity of the skin and releases a small amount of the chemical 203, such as a moisturizer, when held. In an embodiment, a bacteria may be used for microactuation as its humidity level changes.

Implementations of embodiments of the invention may be achieved in different types of electronic devices. For example, a user who has rough skin may have difficulty feeling haptic effects on his/her tablet due to the rough skin. In an embodiment, the electronic device 400 may be in the form of a tablet and include a special coating that includes the chemical 203 that improves a user's sense of touch over time as the user holds the tablet. After a few weeks of use, the user may already start to feel a difference in the haptic feedback provided by the tablet.

In an embodiment, the electronic device 400 may be in the form of a video game controller. As the user is playing a video game on a console, the game controller may suddenly feel very cold as the user's character falls into river. Later, the user's hands may start to burn and tingle as the user's character walks through fire. As the character is hurt and about to die, the user's hand may become numb such that the user has more difficulty operating the controller. The different cooling, burning, tingling and numbing sensations may be generated with different chemicals 203 being delivered by the game controller to the user. In an embodiment, the game controller may become slippery when a game character slips in oil, or sticky when the game character walks through a spiderweb.

In an embodiment, the system 100 may include a tablet and a stylus that the user may use to draw. The haptic feedback provided by the system may replicate the feel of holding a real brush and helps the user draw more precisely. The stylus may include the chemical delivery device and as the user holds the stylus, a small amount of the chemical 203 may be delivered to the surface of the stylus and contact the user's fingers so that a haptic effect that is provided by the system via the tablet or the stylus may feel much sharper and stronger.

In an embodiment, the electronic device 400 may be a smartphone and the user may watch a movie on the smartphone. The user may feel a variety of sensations, such as burning and tingling that seem to match the action in the movie due to the delivery of a suitable chemical 203 through the housing of the smartphone. When such sensations are combined with vibrations generated by the haptic output device 160, the overall effect may be quite realistic and immersive. In an embodiment, the chemical 203 may have properties that provide an embodiment of a smartphone that resists being released by becoming sticky if the user forgets to press "send" on a message, for example.

In an embodiment, the chemical 203 be delivered whenever the hand is in contact with the electronic device 400 to increase tactile sensitivity. In an embodiment, it may be beneficial to control the release of the chemical 203 using the processor 110 of the electronic device 400 to produce tactile sensations at specific moments in a game, for example.

In embodiments, the chemical 203 may be delivered through separate devices that are used with the electronic device that produces the haptic feedback, such as a stylus or the hand rests on a laptop. In an embodiment, the chemical delivery device 170 may be provided to the electronic device 400 in the form of a case or other after-market accessory.

The embodiments described herein represent a number of possible implementations and examples and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

What is claimed is:

1. A system comprising:
    a haptic output device constructed and arranged to generate a haptic effect to a user of the system; and
    a chemical delivery device constructed and arranged to physically deliver a chemical to the user of the system, the chemical having a state selected from the group consisting of a solid, a fluid, and combinations thereof.

2. The system according to claim 1, wherein the haptic output device and the chemical delivery device are separate devices, the system further comprising one or more processors configured to execute at least one computer program module comprising a determination module, when executed by the one or more processors, determines when to initiate delivery of the chemical to change tactile sensitivity of the user and alter the haptic effect generated by the haptic output device.

3. The system according to claim 1, wherein the chemical delivery device comprises a reservoir constructed and arranged to hold the chemical and a positive pressure device constructed and arranged to extract the chemical from the reservoir and deliver the chemical through an opening to the user.

4. The system according to claim 1, wherein the chemical is selected from the group consisting of: a moisturizer, a topical anesthetic, a conductive gel, a pH adjuster, and combinations thereof.

5. The system according to claim 1, wherein the haptic output device comprises the chemical delivery device, and wherein the chemical generates the haptic effect.

6. The system according to claim 5, wherein the haptic effect is a sensation selected from the group consisting of a burning sensation, a warming sensation, a cooling sensation, an itching sensation, a numbing sensation, and combinations thereof.

7. The system according to claim 1, wherein the system is a handheld device selected from the group consisting of a tablet, a smartphone, a game controller, and combinations thereof.

8. The system according to claim 1, further comprising a sensor configured to sense a condition of the user's skin.

9. The system according to claim 8, wherein the condition is humidity.

10. The system of claim 1, wherein the chemical is selected from the group consisting of a powder, gel, liquid, gas, cream, and combination thereof.

11. The system of claim 1, wherein the haptic output device comprises the chemical delivery device.

12. A method to alter a haptic effect felt by a user of an electronic device, the method comprising:
    physically delivering a chemical with a chemical delivery device to the user of the electronic device; and
    generating the haptic effect to the user of the electronic device with a haptic output device.

13. The method according to claim 12, further comprising sensing a condition of the user's skin with a sensor, and determining whether to initiate delivery of the chemical to the user of the electronic device based on the sensed condition with a processor.

14. The method according to claim 13, wherein the condition is humidity.

15. The method according to claim 12, wherein the haptic output device comprises the chemical delivery device, and wherein the chemical generates the haptic effect.

16. The method according to claim 15, wherein the haptic effect is a sensation selected from the group consisting of a burning sensation, a warming sensation, a cooling sensation, an itching sensation, a numbing sensation, and combinations thereof.

17. The method according to claim 12, wherein the chemical is selected from the group consisting of: a moisturizer, a topical anesthetic, a conductive gel, a pH adjuster, and combinations thereof.

18. The method of claim 12, wherein generating the haptic effect comprises physically delivering a chemical with the chemical delivery device.

19. The method of claim 12, wherein physically delivering a chemical with a chemical delivery device comprises delivering a chemical having a state selected from the group consisting of a solid, a fluid, and combinations thereof.

20. The method of claim 19, wherein physically delivering a chemical with a chemical delivery device comprises delivering a chemical selected from the group consisting of a powder, gel, liquid, gas, cream, and combination thereof.

21. The method of claim 12, wherein physically delivering a chemical with a chemical delivery device comprises delivering a chemical to change tactile sensitivity of the user of the electronic device.

\* \* \* \* \*